United States Patent [19]

Schenker et al.

[11] Patent Number: 4,925,587

[45] Date of Patent: May 15, 1990

[54] HYDROXY ETHERS, A PROCESS FOR THEIR PRODUCTION, AND METHODS FOR THEIR USE

[75] Inventors: Gilbert Schenker, Erkrath; Robert Piorr, Ratingen-Hoesel; Sabine Luettge, Monchen-Gladbach, all of Fed. Rep. of Germany

[73] Assignee: Henkel Kommanditgesellschaft auf Aktien, Duesseldorf-Holthausen, Fed. Rep. of Germany

[21] Appl. No.: 219,423

[22] Filed: Jul. 14, 1988

[30] Foreign Application Priority Data

Jul. 15, 1987 [DE] Fed. Rep. of Germany ....... 3723323

[51] Int. Cl.$^5$ .............................................. C11D 1/72
[52] U.S. Cl. ............................. 252/174.22; 252/135; 252/174.21; 252/321; 252/358; 252/DIG. 1; 568/622; 568/616
[58] Field of Search ....................... 252/174.21, 174.22, 252/DIG. 2; 568/618, 622, 678, 679

[56] References Cited

U.S. PATENT DOCUMENTS 3,491,029 1/1970 Kasperl et al. ...................... 252/156
3,696,057 10/1972 Schussler et al. .................... 252/544
4,600,523 7/1986 Piorr et al. ........................ 252/174.22

Primary Examiner—Prince E. Willis
Assistant Examiner—Alexander Ghyka
Attorney, Agent, or Firm—Ernest G. Szoke; Wayne C. Jaeschke; Henry E. Millson, Jr.

[57] ABSTRACT

Hydroxyalkyl polyethylene glycol and hydroxyalkyl polypropylene glycol ethers of the formula

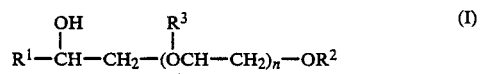

in which $R^1$ is a linear $C_6$–$C_{16}$ alkyl radical, $R^2$ is a linear or branched, $C_1$–$C_{22}$ alkyl or alkenyl radical, $R^3$ is hydrogen or a methyl group, and n is a number of from 0 to 30, and to mixtures of several such compounds. Also, a process for the preparation of these hydroxy ethers, wherein epoxides are reacted with alcohol alkoxylates at an elevated temperature in the presence of a catalyst and in an inert gas atmosphere. The compounds or their mixtures are used as foam inhibiting additives in low-foam cleaning preparations.

19 Claims, No Drawings

HYDROXY ETHERS, A PROCESS FOR THEIR PRODUCTION, AND METHODS FOR THEIR USE

BACKGROUND OF THE INVENTION

1. Field of the Invention

This invention relates to hydroxyalkyl polyethylene glycol and hydroxyalkyl polypropylene glycol ethers, to a process for the production of these compounds, and to their use as foam-inhibiting additives in low-foam cleaning preparations.

2. State of Related Art

Aqueous cleaning preparations intended for use in the institutional and industrial sectors, particularly those intended for cleaning metal, glass, ceramic, and plastic surfaces, generally contain compounds which give rise to undesirable foaming under prevailing working conditions, for example, anionic surfactants or nonionic surfactants which foam at the working temperature. To prevent the unwanted foaming, it is thus necessary in almost every instance to add to aqueous cleaning preparations of the above type substances which are capable of preventing, or reducing the tendency toward, unwanted foaming. In most cases, the use of foaminhibiting additives is also necessary because the soils detached from the substrates and collecting in the cleaning liquors from additional foam.

Adducts of alkylene oxides with organic compounds containing reactive hydrogen atoms, preferably several reactive hydrogen atoms, in the molecule have long been successfully used as foaminhibiting additives. Among such products, adducts of propylene oxide with aliphatic polyalcohols (see e.g. U.S. 3,491,029, and German patent 1 621 593) adducts of propylene oxide with aliphatic polyamines (German patents 1 289 579 and 1 621 593) and also adducts of ethylene oxide and propylene oxide with aliphatic polyamines, particularly ethylenediamine. In addition to a good foam-inhibiting effect, these alkylene oxide adducts also show the alkali stability generally required for use in institutional and industrial cleaning preparations. However, compounds of this type are not sufficiently biodegradable and, accordingly, do not satisfy the current legal requirements of some countries (e.g. regulations under German detergent law).

STATEMENT OF THE INVENTION

Other than in the operating examples, or where otherwise indicated, all numbers expressing quantities of ingredients or reaction conditions used herein are to be understood as modified in all instances by the term "about".

An object of the present invention is to provide foam inhibitors which are easy to produce and which are at least equivalent to, if not even better than, state-of-the-art foam inhibitors with respect to their performance properties. In addition, the invention seeks to provide foam inhibitors which, for low initial foaming, show good staying power, i.e. effectively inhibit foaming at increasing concentrations of test foam generator. In this regard, account had to be taken of the fact that, under waste-water legislation, compounds are required to be substantially biodegradable so that, after introduction into the drainage system, there is no danger of pollution to the wastewaters.

The present invention relates to novel hydroxyalkyl polyethylene glycol and hydroxyalkyl polypropylene glycol ethers corresponding to the following general formula

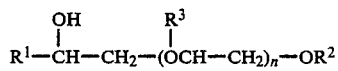

in which
$R^1$ is a linear $C_6$–$C_{16}$ alkyl radical,
$R^2$ is a linear or branched, saturated or unsaturated $C_1$–$C_{22}$ alkyl radical,
$R^3$ is hydrogen or a methyl group and
n is a number of from 0 to 30,
and to mixtures of several such compounds.

The invention also relates to a process for the preparation of the compounds of formula I comprising the steps of (a) reacting an epoxide corresponding to the following general formula

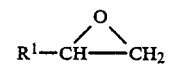

in which $R^1$ is defined above, with an alcohol or alcohol alkoxylate corresponding to the following general formula

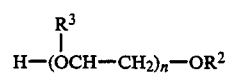

in which $R^2$, $R^3$, and n are as defined above, at an elevated temperature in the presence of a catalyst; the reaction being carried out in an inert gas atmosphere, e.g. a nitrogen atmosphere.

The present invention also relates to the use of the hydroxyalkyl polyethylene glycol and hydroxyalkyl polypropylene glycol ethers of formula I or mixtures thereof as foam-inhibiting additives in low-foam cleaning preparations.

In the compounds of formula I, substituents $R^1$ include the radicals n-hexyl, n-heptyl, n-octyl, n-nonyl, n-decyl, n-undecyl, n-dodecyl, n-tridecyl, n-tetradecyl, n-pentadecyl and n-hexadecyl. The substituent $R^1$ in formula I is preferably a $C_8$–$C_{12}$ alkyl radical.

$R^2$ radicals include methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl and n-docosyl and also the branched-chain isomers of the above-mentioned alkyl radicals. Instead of the saturated alkyl radicals, $R^2$ can also represent unsaturated alkyl radicals containing from 2 to 22 carbon atoms. These unsaturated alkyl radicals (alkenyl radicals) can also be linear or branched.

In one preferred embodiment, $R^2$ represents linear, saturated or unsaturated $C_1$–$C_{22}$ alkyl radicals, of which the linear saturated alkyl radicals containing 1 to 22 carbon atoms are preferred.

Particularly preferred are hydroxyalkyl polyethylene glycol and hydroxyalkyl polypropylene glycol ethers corresponding to formula I in which $R^2$ represents linear, saturated $C_1$–$C_{12}$, and preferably $C_3$–$C_6$, alkyl radicals.

In formula I, $R^3$ is hydrogen or a methyl group, preferably hydrogen compounds wherein at least one $R^3$ is methyl are also within the scope of the invention.

In formula I, n is a number of from 0 to 30, preferably a number of from 1 to 30, more preferably a number of from 1 to 15, and most preferably a number of from 1 to 10. This means that, in the hydroxyalkyl polyethylene glycol and hydroxyalkyl polypropylene glycol ethers of the invention, 0 to 30 ethoxy or propoxy groups, and most preferably 1 to 10 ethoxy or propoxy groups, are incorporated in the molecular chain. However, the ethoxy groups and propoxy groups can be incorporated in the molecular chain in any ratio and in any sequence. Mixed ethers such as these also fall within the scope of formula I.

The compounds of formula I show good biodegradability, and thus satisfy current legal requirements. Accordingly, there is no danger of pollution to wastewaters where the compounds of formula I are used.

However, the greatest advantages of the compounds of the invention is that they show considerable improvement in foaminhibiting effect over hitherto known state-of-the-art compounds. Thus, where the hydroxy ethers of the invention are used, less initial foam is formed than with compounds already known from the prior art. On the other hand, the staying power of the present compounds is also distinctly better.

In the process of the invention for the preparation of the compounds of formula I, the epoxides of formula II are formed from α-olefins, usually monoolefins, obtainable in large quantities by petrochemical methods, by epoxisation reactions known per se, for example reaction of the above olefins with percarboxylic acids or similar epoxide-forming reagents.

Reactants for reaction with the epoxides of formula II are alcohols (when n=0) or alcohol alkoxylates of formula III. The alcohol alkoxylates of formula III are formed from alcohols and olefin epoxides by known methods. The alcohol alkoxylates of formula III are compounds formed from the corresponding alcohols and ethylene oxide or propylene oxide. Preferred reactants for the present process are alcohol alkoxylates corresponding to formula III in which $R^2$ represents linear, saturated or unsaturated $C_1$-$C_{22}$ alkyl radicals, preferably linear saturated $C_1$-$C_{22}$ alkyl radicals. Compounds in which $R^2$ in formula III is a saturated linear $C_1$-$C_{12}$, preferably a $C_3$-$C_6$ alkyl radical, are especially preferred. In the context of the invention, this means that, as educts for the production of the alcohol alkoxylates of formula III to be used in accordance with the invention, it is especially preferred to react $C_3$-$C_6$ alcohols with alkylene oxides, such as ethylene oxide or propylene oxide, in which case the particularly preferred alcohol alkoxylates of general formula III are formed. In this case, therefore, the alcohols include n-propanol, n-butanol, n-pentanol and n-hexanol. Reaction products with ethylene oxide are preferred, so that, in the alcohol alkoxylates III to be used in accordance with the invention, $R^3$ is preferably hydrogen. The reaction ratio, which ultimately also determines the number of alkoxy groups in the molecule of the compounds corresponding to formula III, is more preferably in the range of from 1 : 1 to 1 : 15 so that—where n in general formula III above is not zero—n is a value of from 1 to 15. However, a most preferred range is from 1 to 10.

Alcohol alkoxylates, in which the recurring unit of ethoxy and propoxy groups is in any ratio and in any sequence in the chain, providing the number n for the recurring units is in the above-disclosed range, can also be used in the process of the invention.

In the process of the invention for the production of the compounds of formula I, a molar ratio of approximately 1 : 1 is established in the reaction of II with III. The reaction is carried out at an elevated temperature. According to the invention, this means that the reaction mixture is heated in an inert gas atmosphere to reaction temperatures in the range of from 100° to 180° C., at which the reaction then takes place at an adequate velocity and with a satisfactory yield. A reaction temperature is in range of from 120° to 160° C. is preferred.

According to the invention, the process for the production of the hydroxyalkyl polyethylene glycol and hyroxyalkyl polypropylene glycol ethers corresponding to formula I is carried out in the presence of a catalyst. A quantity of catalyst of from 0.01 to 2.0% by weight, based on the total weight of the reaction mixture, is sufficient for carrying out the reaction. According to the invention, both acidic and basic catalysts can be used. Preferred catalyst systems are alkali metal alcoholates, mineral acids, such as $H_2SO_4$, or Lewis acids, such as $BF_3$ etherate. Sodium methylate is particularly preferred for use in the process of the invention.

The process of the invention is illustrated by the following reaction scheme:

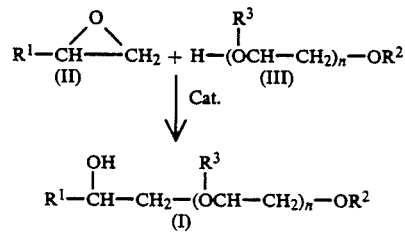

In the above process, not only individual compounds corresponding to formula (I), but also mixtures of such compounds, can be formed in the process of the invention in accordance with the above reaction scheme. Thus, the reaction of the alcohols with alkylene oxides in certain molar ratios does not give an individual compound III, but instead mixtures of various compounds III with a more or less wide distribution of the number of alkoxy groups in thw molecule, i.e. with a more or less wide range for n in formula III. The use of mixtures of the alcohol alkoxylates III in the process of the invention must of course also result in a mixture of compounds I. Mixtures such as these and processes for their production are also covered by the present invention.

Apart from the formation of new and—in relation to the prior art—improved compounds I, the process of the invention has the major advantage over state-of-the-art processes in that, where the described procedure of the invention is used for the production of the hydroxy ethers, reaction times can be reduced to between 0.5 and 1.5 hr. for good product quality and yield. Accordingly, the process of the invention can be carried out quickly and efficiently, producing substantially quantitative yields.

The compounds of formula I or mixtures thereof obtained by the process of the invention are used as foam-inhibiting additives in low-foam cleaning preparations for industrial and institutional purposes. They have the major advantage in such cleaning preparations of combining a quantity of initial foam distinctly below the existing standard with high staying power. The use of the compounds of formula I is also advantageous because the cleaning preparations containing such foam-inhibiting additives satisfy existing legal requirements with respect to biodegradability.

The invention is illustrated but not limited by the following Examples.

EXAMPLES

EXAMPLE 1

354.6 g (3.0 mol) butylglycol and 6.5 g sodium methylate (30% solution in methanol) were heated in vacuo at 60° C. to remove the methanol introduced with the catalyst. After addition of 390.3 g (3.0 mol) 1,2-epoxyoctane (epoxide value 6.4), the mixture was heated for 130 minutes to 160° C. The epoxide value of the product was 0.15 and the OH value 248.6.

EXAMPLE 2

283.9 g (1.75 mol) butyldiglyocl and 7.5 g sodium methylate (30% solution in methanol) were heated in vacuo at 60° C. to remove the methanol. 449.4 g (1.75 mol) 1,2-epoxyhexadecane were added, followed by heating with stirring for 60 minutes to 160° C. The epoxide value of the product was 0.23 and the OH value 143.2.

EXAMPLE 3

355.3 g (1.25 mol) of an adduct of 5 mol ethylene oxide with 1 mol butanol (butanol-5 EO) and 3.3 g sodium methylate (30% solution in methanol) were heated in vacuo at 60° C. to remove the methanol. After addition of 197.0 g (1.25 mol) 1,2-expoydecane the reaction mixture was heated for 15 minutes to 160° C. The epoxide value of the product was 0.11 and the OH value 134.5.

EXAMPLE 4

241.0 g (0.5 mol) butanol-10 EO and 1 g sodium methylate (30% solution in methanol) were evacuated for 10 minutes at 70° C. in a water jet vacuum. 117.6 (0.5 mol) 1,2-epoxytetradecane were added in an inert gas atmosphere, followed by heating for 420 minutes at 110° C. The reaction mixture was then neutralized with a few drops of concentrated sulfuric acid. 348 g of a golden yellow liquid product were obtained. The product had an epoxide value of 0.4, an OH value of 95.8 and a cloud point in water of 16.7° C.

EXAMPLE 5

277.2 g (0.58 mol) butanol-10 EO, 135.2 g (0.58 mol) 1,2-epoxytetradecane and 2.9 g concentrated sulfuric acid were combined and heated upon nitrogen for 370 minutes at 120° C. The reaction mixture was then neutralized with sodium methylate. The epoxide value of the production was 0.16 and the OH value 95.9.

EXAMPLE 6

241.0 g (0.5 mol) butanol-10 EO and 117.6 g (0.5 mol) 1,2-epoxytetradecane were evacuated for 10 minutes at 70° C. The vacuum was removed with argon and 4.3 ml (4.88 g) of a 48% boron trifluoride solution in ether were added. After heating for 15 minutes at 140° C., the reaction mixture was neutralized with sodium methylate solution and filtered. The OH value of the product was 81.9 (theoretical 78.2).

EXAMPLE 7

Further hydroxyalkyl polyethylene glycol and hydroxyalkyl polypropylene glycol ethers of formula I were prepared in the same way as described in Examples 1 to 6 and the products are given in Table 1 below.

TABLE 1

Further compounds corresponding to the formula $$R^1-\underset{\underset{OH}{|}}{CH}-CH_2-(O\underset{\underset{R^3}{|}}{CH}-CH_2)_n-OR^2 \qquad (I)$$

$(R^3 = H^1)$

| Example 7 | $R^1$ | n | $R^2$ | OH value | Epoxide value |
|---|---|---|---|---|---|
| a | $C_{14}H_{29}$ | 5 | (oleyl) | 85 | 0.2 |
| b | $C_{10}H_{21}$ | 9[1] | $C_{12/14}H_{25/29}$ | 90 | 0.2 |
| c | $C_{12}H_{15}$ | 7 | $C_{12/13}H_{25/27}$ | 87 | 0.2 |
| d | $C_{14}H_{29}$ | 7 | $C_{12/13}H_{25/27}$ | 82 | 0.2 |
| e | $C_{10}H_{21}$ | 2 | $C_4H_9$ | 184 | 0.2 |
| f | $C_{12}H_{25}$ | 2 | $C_4H_9$ | 167 | 0.2 |
| g | $C_{14}H_{29}$ | 2 | $C_4H_9$ | 160 | 0.2 |
| h | $C_{16}H_{33}$ | 2 | $C_4H_9$ | 160 | 0.2 |
| i | $C_{16}H_{33}$ | 5 | $C_4H_9$ | 107 | 0.2 |
| j | $C_{12}H_{25}$ | 10 | $C_4H_9$ | 86 | 0.2 |
| k | $C_{14}H_{29}$ | 10 | $C_4H_9$ | 81 | 0.2 |
| l | $C_{16}H_{33}$ | 10 | $C_4H_9$ | 76 | 0.2 |

Explanations:
[1] in the compound Example 7b:
$R^3$ = H or $CH_3$;
molar ratio EO:PO = 4:5

EXAMPLE 8 and COMPARISON EXAMPLES 1 and 2

Testing of foam-inhibiting effect

The foam-inhibiting effect of the hydroxyalkyl polyethylene glycol and hydroxyalkyl polypropylene glycol ethers of formula I according to the invention was measured using a Goette foambeating apparatus standardized in accordance with DIN 53 902. To this end, quantities of 200 ml of a test solution containing 1% by weight sodium hydroxide and 0.03% by weight (300 ppm) of the particular foam inhibitor were tested in the foam-bearing apparatus at 65° C. A 25% by weight solution of the diethanolamine salt of tetrapropylenebenzenesulfonate was added to the solutions in increasing quantities as the test form generator.

The comparison products used (standards) were an adduct of 30 EO and 60 PO with ethylenediamine, commercially available under the name "Genapol ® PN 30" (Hoeschst AG), which shows inadequate biodegradability (Comparison Example 1) and a biodegradable, terminally blocked adduct of ethylene oxide with a fatty alcohol commercially available under the name "Dehypon ® LT 204" (Henkel KGaA) (Comparison Example 2).

The following criteria were used for evaluating the foaminhibiting effect:

1. Initial foam; this must be minimal. For an addition of 1000 ppm test foam generator, the initial foam volume should not exceed 40 ml under the standardized test conditions.

2. The so-called "staying power"; this should be maximal. Staying power is defined as the concentration in ppm of test foam generator at which the foam volume amounts to or exceeds 300 ml under the standardized conditions and for a given concentration of foam inhibitor. The staying power should amount to at least 1800 ppm (this corresponds to the value obtained with the comparison products).

To test the foam-inhibiting effect, the foam volume (in ml) was read off every 5 second after a series of 500 beats. An average value was determined from five individual measurements.

The test results are shown in Table 2 below.

TABLE 2

| Example | Initial foam (ml) | Staying power (ppm test foam generator) |
|---|---|---|
| 7a | 20 | 2,400 |
| 7b | 20 | 2,200 |
| 7c | 30 | 2,000 |
| 7d | 30 | 2,400 |
| 7e | 30 | 2,600 |
| 7f | 30 | 4,200 |
| 7g | 20 | 3,200 |
| 7h | 40 | 3,600 |
| 7i | 15 | 1,800 |
| 7j | 30 | 2,000 |
| 7k | 30 | 1,800 |
| 7l | 35 | 1,800 |
| Comp. 1 | 30 | 1,800 |
| Comp. 2 | 40 | 1,800 |

Result

As can be seen from Table 2, the hydroxy mixed ethers of general formula I according to the invention show distinctly better results than hitherto known foam inhibitors with respect to initial foam value and staying power.

We claim:

1. A composition of the formula $$R^1-\underset{\underset{OH}{|}}{CH}-CH_2-(O\underset{\underset{R^3}{|}}{CH}-CH_2)_n-OR^2 \qquad (I)$$

wherein
 $R^1$ is a linear $C_6$-$C_{16}$ alkyl radical,
 $R^2$ is a linear or branched, $C_1$-$C_{22}$ alkyl or alkenyl radical
 $R^3$ is hydrogen or a methyl group wherein at least one $R^3$ is hydrogen and at least one $R^3$ is methyl, and
 n is a number of from 2 to 30.

2. A compound of claim 1 wherein $R^1$ is a linear $C_8$-$C_{12}$ alkyl radical.

3. A compound of claim 1 wherein $R^2$ is a linear alkyl or alkenyl radical.

4. A compound of claim 1 wherein $R^2$ is a linear $C_1$-$C_{12}$ alkyl radical.

5. A compound or claim 1 wherein $R^2$ is a linear $C_3$-$C_6$ *alkyl radical.*

6. A compound of claim 1 wherein n is a number of from 2 to 15.

7. A compound of claim 1 wherein n is a number of from 2 to 10.

8. A compound of claim 1 wherein $R^1$ is a linear $C_8$-$C_{12}$ alkyl radical, and $R^2$ is a linear $C_1$-$C_{12}$ alkyl radical.

9. The compound of claim 8 wherein $R^2$ is a linear $C_3$-$C_6$ alkyl radical.

10. In a low-foam cleaning composition, the improvement comprising the presence therein of a foam-inhibiting quantity of the composition of claim 1.

11. A compound of the formula:

$$R^1-\underset{\underset{OH}{|}}{CH}-CH_2-(O\underset{\underset{R^3}{|}}{CH}-CH_2)_n-OR^2 \qquad (I)$$

wherein
 $R^1$ is a linear $C_6$-$C_{16}$ alkyl radical,
 $R^2$ is a linear or branched, $C_2$-$C_{22}$ alkenyl radical,
 $R^3$ is a hydrogen or a methyl group, and
 n is a number of from 1 to 30, and to mixtures of two or more compounds of formula I.

12. A compound of claim 11 wherein $R^2$ is a linear alkenyl radical.

13. A compound of claim 11 wherein $R^2$ is a linear $C_2$-$C_{12}$ alkenyl radical.

14. A compound of claim 11 wherein $R^2$ is a linear $C_3$-$C_6$ alkenyl radical.

15. A compound or claim 11 wherein $R^3$ is hydrogen.

16. A compound of claim 11 wherein n is a number of from 1 to 15.

17. A compound of claim 11 wherein n is a number of from 1 to 10.

18. A compound of claim 11 wherein $R^1$ is a linear $C_8$-$C_{12}$ alkyl radical.

19. A compound of claim 1 wherein in the $$-(O\underset{\underset{R^3}{|}}{CH}-CH_2)_n-$$

moiety, at least one $R^3$ is hydrogen, and at least on $R^3$ group is methyl.

* * * * *